(12) United States Patent
Lee et al.

(10) Patent No.: US 12,605,121 B2
(45) Date of Patent: Apr. 21, 2026

(54) APPARATUS AND METHOD FOR ESTIMATING BIO- INFORMATION

(71) Applicant: SAMSUNG ELECTRONICS CO., LTD., Suwon-si (KR)

(72) Inventors: June Young Lee, Seongnam-si (KR); Bok Soon Kwon, Seoul (KR); Jeong Yun Seo, Suwon-si (KR); Woo Chang Lee, Anyang-si (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 926 days.

(21) Appl. No.: 17/670,069

(22) Filed: Feb. 11, 2022

(65) Prior Publication Data

US 2023/0157645 A1 May 25, 2023

(30) Foreign Application Priority Data

Nov. 19, 2021 (KR) ........................ 10-2021-0159954

(51) Int. Cl.
*A61B 5/00* (2006.01)

(52) U.S. Cl.
CPC .......... *A61B 5/7275* (2013.01); *A61B 5/0075* (2013.01)

(58) Field of Classification Search
CPC .. G01N 21/31; A61B 5/0205; A61B 5/02416; A61B 5/681; A61B 5/7275;
(Continued)

(56) References Cited

U.S. PATENT DOCUMENTS

| | | | |
|---|---|---|---|
| 5,137,023 A | 8/1992 | Mendelson et al. | |
| 6,714,805 B2 | 3/2004 | Jeon et al. | |

(Continued)

FOREIGN PATENT DOCUMENTS

| | | |
|---|---|---|
| CN | 105092436 B | 1/2018 |
| CN | 109100315 A | 12/2018 |

(Continued)

OTHER PUBLICATIONS

Beć KB. A Simple guide to complex world of overtone and combination bands: Theoretical simulation and interpretation of NIR spectra—summary of the workshop at NIR-2021 Beijing Conference. NIR news. 2021;32(7-8):15-18. doi: 10.1177/09603360211060966 (Year: 2021).*

(Continued)

*Primary Examiner* — Patrick Fernandes
*Assistant Examiner* — Melissa Jo Montgomery
(74) *Attorney, Agent, or Firm* — Sughrue Mion, PLLC

(57) ABSTRACT

An apparatus and method for estimating bio-information are provided. The apparatus for estimating bio-information includes: a spectrometer configured to measure a spectrum from an object according to measurement conditions; and a processor configured to obtain signal-to-noise ratio (SNR) values for each wavelength of the spectrum measured by the spectrometer, generate a plurality of simulated absorbance spectra based on the SNR values for each wavelength of the spectrum, and determine an optimal wavelength combination for use in measuring the bio-information based on the plurality of simulated absorbance spectra.

18 Claims, 12 Drawing Sheets

(58) Field of Classification Search
CPC . A61B 5/1455; A61B 5/6802; A61B 5/14532; A61B 5/0075; A61B 5/0002; A61B 5/02438
See application file for complete search history.

(56) References Cited

U.S. PATENT DOCUMENTS

| | | | |
|---|---|---|---|
| 7,460,895 B2 | 12/2008 | Arnold et al. | |
| 7,830,519 B2 | 11/2010 | Mah et al. | |
| 7,962,187 B2 | 6/2011 | Fantini | |
| 9,654,745 B2 | 5/2017 | Zeng et al. | |
| 10,809,184 B1 * | 10/2020 | Prater | G01J 3/4535 |
| 2005/0020892 A1 | 1/2005 | Acosta et al. | |
| 2005/0149300 A1 | 7/2005 | Ruchti et al. | |
| 2009/0198113 A1 | 8/2009 | Rensen et al. | |
| 2011/0009720 A1 | 1/2011 | Kunjan et al. | |
| 2019/0033135 A1 | 1/2019 | Haider et al. | |
| 2019/0128934 A1 * | 5/2019 | Park | G01R 23/163 |
| 2021/0404875 A1 | 12/2021 | Schwab et al. | |

FOREIGN PATENT DOCUMENTS

| | | | |
|---|---|---|---|
| WO | 2005/099567 A2 | 10/2005 | |
| WO | 2005/103945 A2 | 11/2005 | |
| WO | 2020/076844 A1 | 4/2020 | |

OTHER PUBLICATIONS

NIR News Conference Article (Year: 2021).*

Hazen et al., "Measurement of Glucose in Water with First-Overtone Near-Infrared Spectra," Abstract, Applied Spectroscopy, vol. 52, Issue 12, pp. 1597-1605, 1998 (total 4 pages).

Communication dated Aug. 10, 2022 issued by the European Patent Office in European Application No. 22161321.9.

Su et al., "Monolithic on-chip mid-IR methane gas sensor with waveguide-integrated detector", Applied Physics Letters, Feb. 7, 2019, 5 total pages, doi:10.1063/1.5053599.

Dankowska et al., "Detection of plant oil addition to cheese by synchronous fluorescence spectroscopy", Dairy Science & Technology, Mar. 15, 2015, pp. 413-424, vol. 95, doi:10.1007/s13594-015-0218-5.

Communication dated Jan. 16, 2026, issued by Korean Ministry of Intellectual Property in Korean Patent Application No. 10-2021-0159954.

* cited by examiner

900

910

APPARATUS AND METHOD FOR ESTIMATING BIO- INFORMATION

CROSS-REFERENCE TO RELATED APPLICATION(S)

This application claims priority from Korean Patent Application No. 10-2021-0159954, filed on Nov. 19, 2021, in the Korean Intellectual Property Office, the disclosure of which is incorporated by reference herein in its entirety.

BACKGROUND

1. Field

The present disclosure relates to an apparatus and method for non-invasively estimating bio-information.

2. Description of Related Art

Recently, there has been research on methods of non-invasively estimating bio-information, such as blood glucose, using Raman Spectroscopy or a near-infrared spectrometer. In the methods of estimating bio-information, a spectrum is measured from an object using a spectrometer, and bio-information is estimated based on the measured spectrum. The spectrum generally includes a light source for emitting light onto the object, such as a human body, and a detector for detecting an optical signal returning from the object. A broadband light source has been used as a light source, but recently, a laser spectrometer using tunable laser or a laser array as a light source is used.

SUMMARY

According to an aspect of an example embodiment, there is provided an apparatus for estimating bio-information, the apparatus including: a spectrometer configured to measure a spectrum from an object according to measurement conditions; and a processor configured to obtain signal-to-noise ratio (SNR) values for each wavelength of the spectrum measured by the spectrometer, generate a plurality of simulated absorbance spectra based on the SNR values for each wavelength of the spectrum, and determine an optimal wavelength combination for use in measuring the bio-information based on the plurality of simulated absorbance spectra.

The spectrometer may include a light source configured to radiate light onto the object, and a detector configured to detect an optical signal by receiving light scattered or reflected from the object.

The measurement conditions may include at least one of an optical path length, a light source intensity for each wavelength of the spectrum, and detector noise characteristics for each wavelength of the spectrum.

The processor may be further configured to obtain noise equivalent absorbance for each wavelength of the spectrum based on the SNR values for each wavelength of the spectrum, and generate the plurality of simulated absorbance spectra based on the noise equivalent absorbance for each wavelength of the spectrum.

The processor may be further configured to obtain, based on the plurality of simulated absorbance spectra, prediction values of a target component for each of a plurality of predetermined wavelength combinations.

The processor may be further configured to obtain the prediction values of the target component for each of the plurality of predetermined wavelength combinations by using at least one of linear regression analysis and component analysis by classical least squares (CLS).

The processor may be further configured to obtain measurement performance for each of the plurality of predetermined wavelength combinations based on the prediction values for each of the plurality of predetermined wavelength combinations, and determine the optimal wavelength combination for use in the measuring of the bio-information based on the measurement performance for each of the plurality of predetermined wavelength combinations.

The processor may be further configured to obtain Limit of Detection (LoD) values as the measurement performance.

The processor may be further configured to obtain the LoD values based on at least one of a mean value and a standard deviation of the prediction values for each of the plurality of predetermined wavelength combinations.

The processor may be further configured to obtain, based on the LoD values for each of the plurality of predetermined wavelength combinations, a statistical value of the LoD values for each of the plurality of predetermined wavelength combinations, and determine the optimal wavelength combination in ascending order of the LoD values for each of the plurality of predetermined wavelength combinations.

The processor may be further configured to estimate the bio-information using the optimal wavelength combination.

The optimal wavelength combination may be included in at least one of a combination band region and an overtone band region.

According to an aspect of an example embodiment, there is provided a method of estimating bio-information, the method including: measuring a spectrum from an object according to measurement conditions; obtaining signal-to-noise ratio (SNR) values for each wavelength of the spectrum; generating a plurality of simulated absorbance spectra based on the SNR values for each wavelength of the spectrum; and determining an optimal wavelength combination for use in measuring the bio-information based on the plurality of simulated absorbance spectra.

The measurement conditions may include at least one of an optical path length, a light source intensity for each wavelength of the spectrum, and detector noise characteristics for each wavelength of the spectrum.

The generating of the plurality of simulated absorbance spectra may include obtaining noise equivalent absorbance for each wavelength of the spectrum based on the SNR values for each wavelength of the spectrum; and generating the plurality of simulated absorbance spectra based on the noise equivalent absorbance for each wavelength of the spectrum.

The determining of the optimal wavelength combination may include obtaining prediction values of a target component for each of a plurality of predetermined wavelength combinations, based on the plurality of simulated absorbance spectra.

The determining of the optimal wavelength combination may include obtaining measurement performance for each of the plurality of predetermined wavelength combinations based on the prediction values for each of the plurality of predetermined wavelength combinations; and determining the optimal wavelength combination for use in the measuring of the bio-information based on the measurement performance for each of the plurality of predetermined wavelength combinations.

The method may further include obtaining Limit of Detection (LoD) values as the measurement performance, and the determining of the optimal wavelength combination may include obtaining the LoD values based on at least one of a mean value and a standard deviation of the prediction values for each of the plurality of predetermined wavelength combinations.

The determining of the optimal wavelength combination may include obtaining a statistical value of the LoD values for each of the plurality of predetermined wavelength combinations, based on the LoD values for each of the plurality of predetermined wavelength combinations; and determining the optimal wavelength combination in ascending order of the LoD values for each of the plurality of predetermined wavelength combinations.

The optimal wavelength combination may be included in at least one of a combination band region and an overtone band region.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
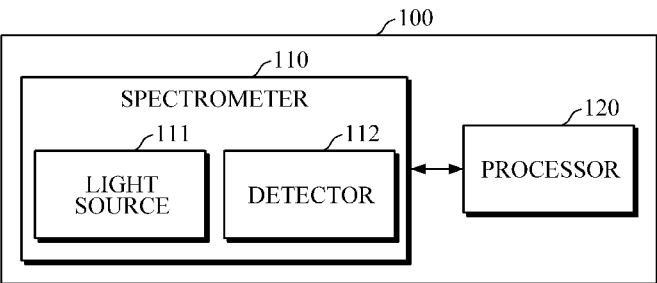
FIG. 1 is a block diagram illustrating a spectrometer according to an example embodiment.

Details of other embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for estimating bio-information will be described in detail with reference to the accompanying drawings.

FIG. 1 is a block diagram illustrating an apparatus for estimating bio-information according to an example embodiment. An apparatus 100 for estimating bio-information may be mounted in a wearable device worn by a user. For example, the wearable device may be formed in various types, such as a wristwatch-type wearable device, a bracelet-type wearable device, a wristband-type wearable device, a ring-type wearable device, a glasses-type wearable device, a headband-type wearable device, etc. That is, the wearable device is not limited herein to a particular type and/or size.

Referring to FIG. 1, the apparatus 100 for estimating bio-information includes a spectrometer 110 and a processor 120. In some embodiments, the bio-information may include an antioxidant level (e.g., carotenoid), blood glucose, blood pressure, lactate, alcohol, cholesterol, triglyceride, etc., but is not limited thereto. The following description will be given using blood glucose as an example of the bio-information.

The spectrometer 110 may measure a spectrum from an object. For example, various spectrometers, such as a laser spectrometer, an infrared spectrometer, a Raman spectrometer, etc., may be used as the spectrometer 110. For convenience of explanation, the following description will be given using a laser spectrometer as an example. The object may be a skin of a user (e.g., skin located at an upper part of the wrist where veins or capillaries are located or the skin surface of the wrist that is adjacent to the radial artery), or peripheral parts of the body of the user, such as fingers, toes, earlobes, and the like, where blood vessels are densely distributed. However, the object is not limited thereto.

The spectrometer 110 may be a laser spectrometer and may include a light source 111 and a detector 112. The light source 111 may emit light onto the object, and the detector 112 may detect an optical signal by receiving light scattered or reflected from the object.

The light source 111 may be formed as laser, e.g., tunable laser, a laser array, and the like. However, the light source 111 is not limited thereto and may be formed as a light emitting diode (LED), a laser diode (LD), a phosphor, etc., and may emit light in a Near Infrared Ray (NIR) or Mid Infrared Ray (MIR) range. Once the light source 111 emits light onto the skin of the user as the object according to a control signal of the processor 120, the emitted light may penetrate through the skin of the user into body tissue, and after reaching the body tissue, the light may be scattered or reflected from the body tissue of the user to return through the skin of the user.

The detector 112 may measure a spectrum by detecting the light that returns through the skin of the user. In some embodiments, the detector 112 may include a photodiode, a photodiode array, a photo transistor (PTr), and the like. However, the detector 112 is not limited thereto, and may include a complementary metal-oxide semiconductor (CMOS) image sensor, a charge-coupled device (CCD) image sensor, and the like.

In response to input of measurement conditions, the spectrometer 110 may measure a spectrum from the object. For example, the measurement conditions may include an optical path length, a light source intensity for each wavelength of the spectrum or detector noise characteristics for each wavelength of the spectrum, but are not limited thereto. For example, the optical path length may vary depending on optical coefficients, such as scattering, absorption, and anisotropy of skin, etc., which are characteristics of the object to be measured, and the light source intensity for each wavelength or the detector noise characteristics for each wavelength may be changed due to a change in device characteristics of the spectrometer 110. Accordingly, by reflecting these data as measurement conditions, the spectrum may be measured from the object.

The processor 120 may be electrically connected (e.g., communicatively coupled) to the spectrometer 11. In response to a request of a user, the processor 120 may control the spectrometer 110 and may receive the measured spectrum from the spectrometer 110.

Generally, the spectrometer 110 provides no method of selecting a wavelength to be used. In the case where many wavelengths are used during measurement, selectivity increases such that the limit of detection is improved. However, when there is a limited time for measuring the object, the use of many wavelengths may lead to a decrease in measurement time at individual wavelengths, such that both the selectivity and the limit of detection decrease at the same time. Accordingly, in order to maximize the limit of detection within a limited measurement time, there is a need for a method for selecting an optimal wavelength for use in measurement.

The processor 120 may calculate a signal-to-noise ratio (SNR) for each wavelength of the spectrum measured by the spectrometer 110, and based on the calculated SNR for each wavelength, the processor 120 may determine an optimal wavelength combination for use in measuring bio-information.

Figure 2A:
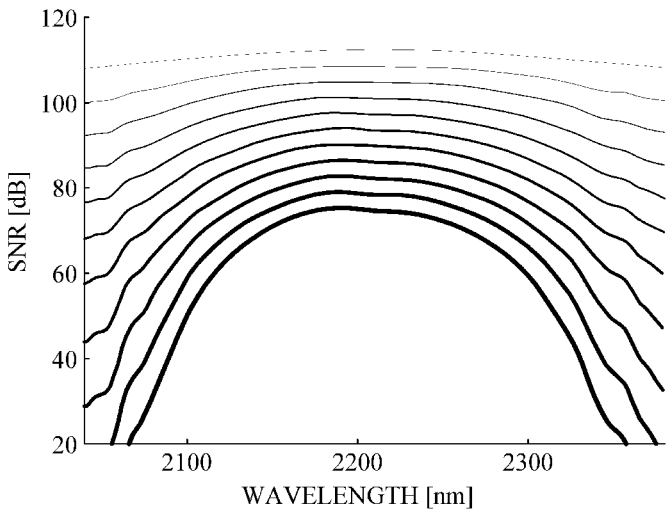
FIGS. 2A and 2B are diagrams illustrating an example of calculating SNR values for each wavelength according to an optical path length, according to an example embodiment.
Figure 2B:
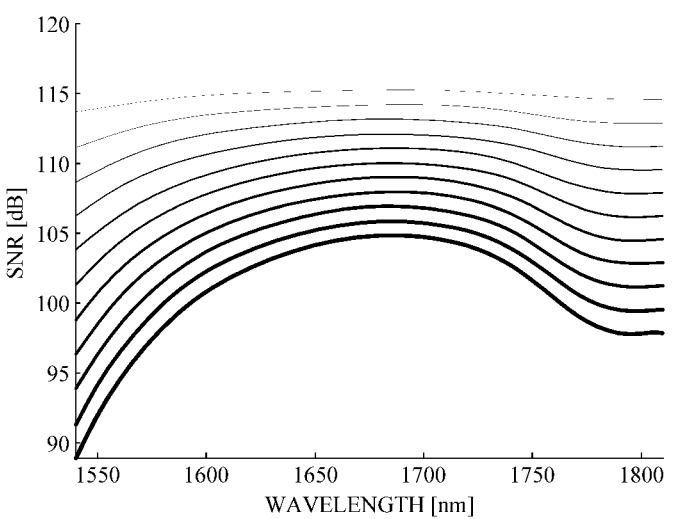

FIGS. 2A and 2B are diagrams illustrating an example of calculating SNR values for each wavelength according to an optical path length.

FIG. 2A illustrates SNR values calculated, for example, in a combination band region. FIG. 2B illustrates SNR values calculated, for example, in an overtone band region. The combination band corresponds to a wavelength range of 2040 nm to 2380 nm, and the overtone band corresponds to a wavelength range of 1540 nm to 1820 nm. The two bands are mainly used as wavelength ranges for a spectrometer 110. The SNR represents a signal-to-noise ratio, which generally indicates a ratio between signal power and noise power.

In FIGS. 2A and 2B, a spectrum at the top shown as a thin line indicates a short optical path length; and a spectrum at the bottom shown as a thick line indicates a long optical path length. That is, if the optical path length is short, a distance to an object is short, resulting in low optical loss and a high SNR. If the optical path length is long, a distance to an object is long, resulting in high optical loss and a low SNR. For example, the processor 120 may obtain SNR values for each wavelength based on a predetermined optical path length in the combination band region of FIG. 2A, in the overtone band region of FIG. 2B, or in a region including both the combination band and overtone band regions.

Alternatively or additionally, the processor 120 may generate a plurality of simulated absorbance spectra based on the calculated SNR values for each wavelength. For example, the processor 120 may obtain Noise Equivalent Absorbance (NEA) for each wavelength based on the SNR values for each wavelength, and may generate the plurality of simulated absorbance spectra based on the obtained NEA for each wavelength.

The limits of detection can be quantified as the NEA which may be calculated by the following Eq. 1.

$$NEA = \log_{10} e/SNR \qquad \text{[Equation 1]}$$

As shown in the above Equation 1, the processor 120 may obtain the NEA for each wavelength using the SNR for each wavelength as the denominator.

The processor 120 may obtain the plurality of simulated absorbance spectra by applying the NEA for each wavelength to the spectra, and may be calculated using, for example, the following Equation 2.

$$SAS = BS \times L + TS \times C \times L + NEA \times random(-1 \sim 1) \qquad \text{[Equation 2]}$$

In this case, SAS denotes the simulated absorbance spectra (SAS); BS denotes a background spectrum, e.g., a water spectrum or skin spectrum; TS denotes a target spectrum; L denotes the optical path; and C denotes a predetermined concentration of a target component, and a low concentration, for example, 50 mg/dl glucose, may be set as a fixed value. In the above Equation 2, the simulated absorbance spectra are obtained by multiplying the NEA by a random number within a predetermined range of, for example, from −1 to 1, such that the processor 120 may obtain the plurality of simulated absorbance spectra. The predetermined range is not specifically limited thereto.

The processor 120 may obtain, using the plurality of simulated absorbance spectra, a plurality of prediction values of a target component for each of a plurality of predetermined wavelength combinations. For example, the processor 120 may obtain concentration prediction values of a target component using linear regression analysis or component analysis by classical least squares (CLS).

For example, a user of the spectrometer 110 may set any number of wavelength combinations based on an object position, bio-information to be estimated, etc., and may also determine any number of wavelengths in the wavelength combinations. For example, the user of the spectrometer 110 may set the combination band region, the overtone band region, or a region including both the combination band and overtone band regions as the wavelength combinations, such that an optimal wavelength combination determined by the processor 120 may be a wavelength combination in at least one region among the combination band region, the overtone band region, and a region including both the combination band and overtone band regions.

The processor 120 may calculate measurement performance for each wavelength combination based on the plurality of prediction values obtained for each wavelength combination, and may derive an optimal wavelength combination for use in measurement based on the calculated measurement performance for each wavelength. For example, the processor 120 may calculate the limits of detection (LoD) as the measurement performance for each wavelength combination. For example, the processor 120 may calculate a mean value or a standard deviation of the respective prediction values for each wavelength combination, and may calculate the LoD for each wavelength based on the calculated value.

The LoD is defined as the lowest quantity of a predetermined component that can be detected. The LoD is generally used to show measurement performance of a biological component, and a lower LoD shows a better measurement performance. For example, the processor 120 may obtain the LoD using the following Equation 3.

$$LoD=LoB+1.645\times\sigma s \qquad \text{[Equation 3]}$$

Herein, the Limit of Blank (LoB) denotes the LoD of a component in a blank sample with no target concentration being contained, such as water; and $\sigma s$ denotes the standard deviation of the respective prediction values. The processor 120 may obtain the LoD for each wavelength by multiplying the LoD value for the blank sample and the standard deviation of the respective prediction values by 1.645 and by adding up the values.

The processor 120 may determine the optimal wavelength combination based on the calculated LoD values for each wavelength combination. For example, the processor 120 may calculate a statistical value (e.g., mean value) of the LoD values for each wavelength combination, and may determine the optimal wavelength combination in ascending order of the calculated statistical values for each wavelength combination.

Figure 3A:
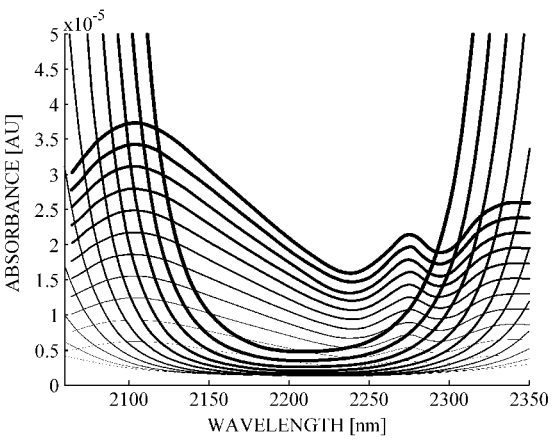
FIGS. 3A and 3B are diagrams illustrating NEA and a glucose spectrum according to an optical path length, according to an example embodiment.
Figure 3B:
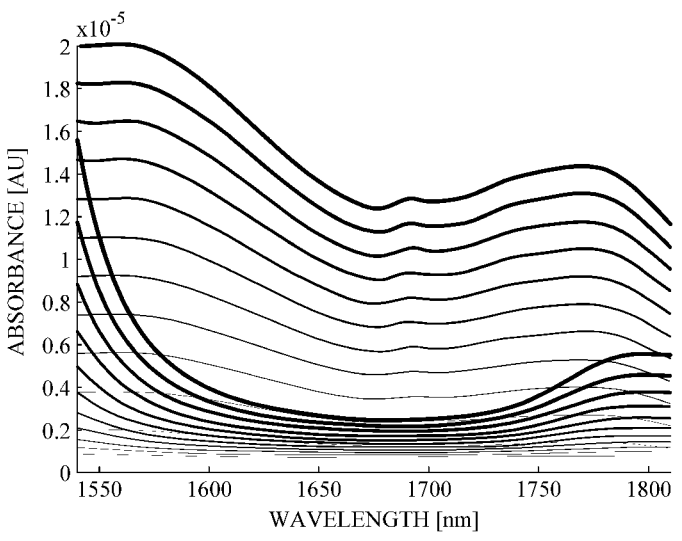

FIG. 3A is a diagram illustrating NEA and a glucose spectrum according to an optical path length in, for example, a combination band region. FIG. 3B is a diagram illustrating NEA and a glucose spectrum according to an optical path length in, for example, the overtone band region. In FIGS. 3A and 3B, a U-shaped spectrum denotes the NEA, and a spectrum on top of the U-shaped spectrum shows the glucose spectrum. The NEA or the glucose spectrum, both shown as thick lines, indicate spectra of a long optical path, and spectra shown as thin lines indicate spectra of a short optical path. The processor 120 may obtain the NEA for each wavelength based on a predetermined optical path length, and may obtain the plurality of simulated absorbance spectra by a linear combination of the obtained NEA and glucose spectrum for each wavelength.

Figure 4:
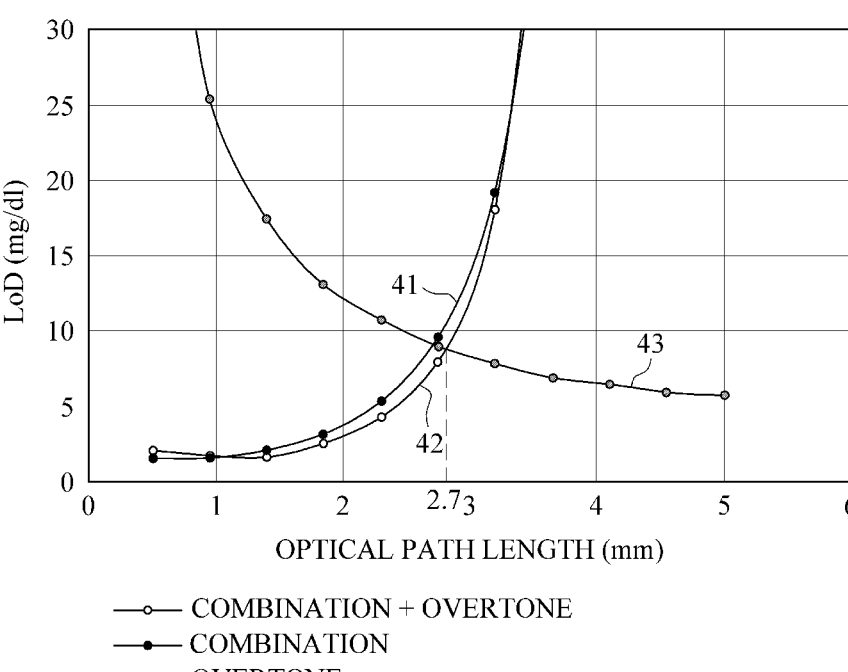
FIG. 4 is a diagram illustrating LoD values according to an optical path length for a plurality of wavelength regions.

FIG. 4 is a diagram illustrating LoD values according to an optical path length for a plurality of wavelength regions, in which curves indicate a combination band region 41, an overtone band region 43, and a region 42 including both the combination band and overtone band regions. Referring to FIG. 4, under measurement conditions set for the spectrometer 110, e.g., a condition that an optical path length is about 1 mm or less, the processor 120 may determine, as an optimal wavelength combination, a wavelength combination in the combination band region 41 having a relatively low LoD value. Further, in the case where the optical path length is from 1 mm to 2.7 mm, the processor 120 may determine, as an optimal wavelength combination, a wavelength combination in the region 42 including the combination band and overtone band regions having a relatively low LoD value; and in the case where the optical path length is equal to or greater than 2.7 mm, the processor 120 may determine, as an optimal wavelength combination, a wavelength combination in the overtone band region 43 having a relatively low LoD value.

The processor 120 may estimate bio-information using the derived optimal wavelength combination. For example, the processor 120 may extract feature values for each wavelength included in the optimal wavelength combination, and may estimate blood glucose using the extracted feature values and a predefined blood glucose estimation model. In this case, the predefined blood glucose estimation model may be defined as various linear or non-linear combination functions, such as addition, subtraction, division, multiplication, logarithmic value, regression equation, and the like, with no specific limitation.

Figure 5:
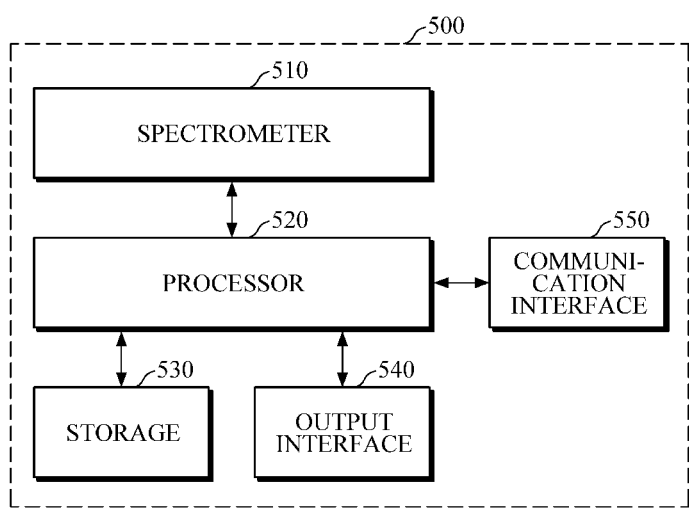
FIG. 5 is a block diagram illustrating an apparatus for estimating bio-information according to another example embodiment.

FIG. 5 is a block diagram illustrating an apparatus for estimating bio-information according to an example embodiment of the present disclosure.

Referring to FIG. 5, an apparatus 500 for estimating bio-information may include a spectrometer 510, a processor 520, a storage 530, an output interface 540, and a communication interface 550. The apparatus 500 may include and/or may be similar in many respects to the apparatus 100 described above with reference to FIG. 1, and may include additional features not mentioned above. Furthermore, the spectrometer 510 and the processor 520 may include and/or may be similar in many respects to the spectrometer 110 and the processor 120 described above with reference to FIG. 1, respectively, and may include additional features not mentioned above. Consequently, repeated descriptions of the apparatus 500, the spectrometer 510, and the processor 520 described above with reference to FIG. 1 may be omitted for the sake of brevity.

The storage 530 may store information related to estimating bio-information. For example, the storage 530 may store processing results of the processor 520, such as the SNR for each wavelength, the NEA for each wavelength, the simulated absorbance spectra, and the like.

The storage 530 may include at least one storage medium of a flash memory type memory, a hard disk type memory, a multimedia card micro type memory, a card type memory (e.g., a secure digital (SD) memory card, an extreme digital (XD) memory card, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 540 may provide processing results of the processor 520 to a user. For example, the output interface 540 may display an estimated blood glucose value of the processor 520 on a display. In this case, if the estimated blood glucose value falls outside a normal range, the output interface 540 may provide the user with warning information by changing color, line thickness, etc., or displaying an abnormal value along with a normal range, so that the user may easily recognize the abnormal value. Further, the output interface 540 may provide the user with the estimated blood glucose value in a non-visual manner by voice, vibrations, tactile sensation, and the like using an audio output module, such as a speaker, or a haptic module and the like.

The communication interface 550 may communicate with an external device to transmit and receive various data related to estimating bio-information. The external device may include an information processing device such as a smartphone, a tablet personal computer (PC), a desktop computer, a laptop computer, and the like. For example, the communication interface 550 may transmit a blood glucose estimation result to the external device, such as a smartphone of the user and the like, so that the user may manage and monitor component analysis results using a device having a relatively high performance.

The communication interface 550 may communicate with the external device using various wired or wireless communication techniques, such as BLUETOOTH® communication, BLUETOOTH® Low Energy (BLE) communication, Near Field Communication (NFC), wireless local area network (WLAN) communication, Zigbee communication, Infrared Data Association (IrDA) communication, Wi-Fi Direct (WFD) communication, Ultra-Wideband (UWB) communication, Ant+ communication, wireless-fidelity (Wi-Fi) communication, Radio Frequency Identification (RFID) communication, 3G, 4G, and 5G communications, and the like. However, this is merely exemplary and is not intended to be limiting.

Figure 6:
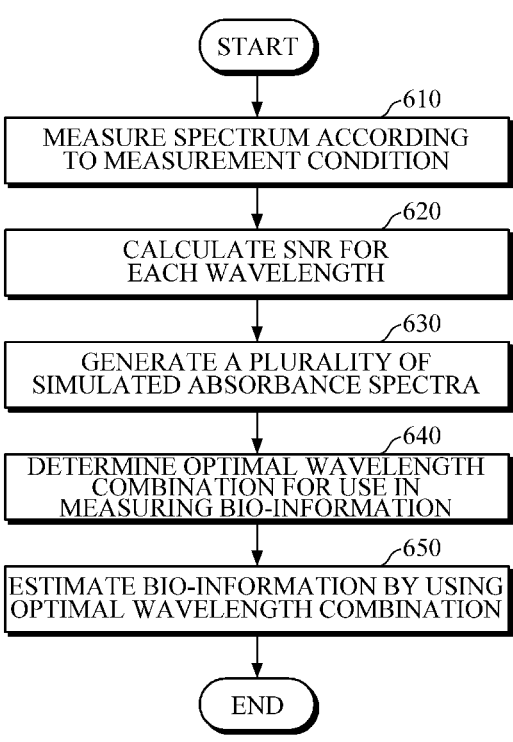
FIG. 6 is a flowchart illustrating a method of estimating bio-information according to an example embodiment.

FIG. 6 is a flowchart illustrating a method of estimating bio-information according to an example embodiment of the present disclosure.

The method of FIG. 6 may be an example of a method of estimating bio-information performed by the apparatuses 100 and 500 for estimating bio-information in the embodiments of FIGS. 1 and 5, which are described in detail above, and thus will be briefly described below in order to avoid redundancy.

Referring to FIG. 6, the apparatus for estimating bio-information may first measure a spectrum from an object according to measurement conditions in operation 610. The measurement conditions may include at least one of an optical path length, a light source intensity for each wavelength, and detector noise characteristics for each wavelength.

The apparatus for estimating bio-information may calculate SNR values for each wavelength of the measured spectrum in operation 620. For example, the apparatus for estimating bio-information may obtain the SNR values for each wavelength based on a predetermined optical path length in a combination band region, an overtone band region, or a region including both the combination band and overtone band regions.

The apparatus for estimating bio-information may generate a plurality of simulated absorbance spectra based on the calculated SNR values for each wavelength in operation 630. For example, the apparatus for estimating bio-information may obtain noise equivalent absorbance for each wavelength based on the SNR values for each wavelength, and may generate a plurality of simulated absorbance spectra based on the obtained noise equivalent absorbance for each wavelength. The limits of detection can be quantified as the NEA for each wavelength, and the NEA may be obtained by Equation 1 using the SNR for each wavelength as the denominator.

The apparatus for estimating bio-information may derive an optimal wavelength combination for use in measuring bio-information based on the generated plurality of simulated absorbance spectra in operation 640. For example, using the respective simulated absorbance spectra, the apparatus for estimating bio-information may obtain a plurality of prediction values of a target component for each of a plurality of predetermined wavelength combinations. For example, a user of the spectrometer may set any number of wavelength combinations based on an object position, bio-information to be estimated, etc., and may also determine any number of wavelengths in the wavelength combinations.

Alternatively or additionally, the apparatus for estimating bio-information may calculate measurement performance for each wavelength combination based on the obtained plurality of prediction values for each wavelength combination, and may derive an optimal wavelength combination for use in measurement based on the calculated measurement performance for each wavelength combination. For example, the apparatus for estimating bio-information may calculate the LoD values for each wavelength combination as the measurement performance, may calculate a mean value or a standard deviation of the respective prediction values for each wavelength combination, and may calculate the LoD values for each wavelength combination based on the calculated value.

In some embodiments, the apparatus for estimating bio-information may determine the optimal wavelength combination based on the calculated LoD values for each wavelength combination. For example, the apparatus for estimating bio-information may calculate a statistical value (e.g., mean value) of the LoD values for each wavelength combination, and may determine the optimal wavelength combination in ascending order of the calculated statistical values of the LoD values for each wavelength combination.

The apparatus for estimating bio-information may estimate bio-information using the optimal wavelength combination in operation 650. For example, the apparatus for estimating bio-information may extract feature values for each wavelength included in the optimal wavelength combination, and may estimate blood glucose using the extracted feature values and a predefined blood glucose estimation model. For example, the predefined blood glucose estimation model may be defined as various linear or non-linear combination functions, such as addition, subtraction, division, multiplication, logarithmic value, regression equation, and the like, with no specific limitation.

Figure 7:
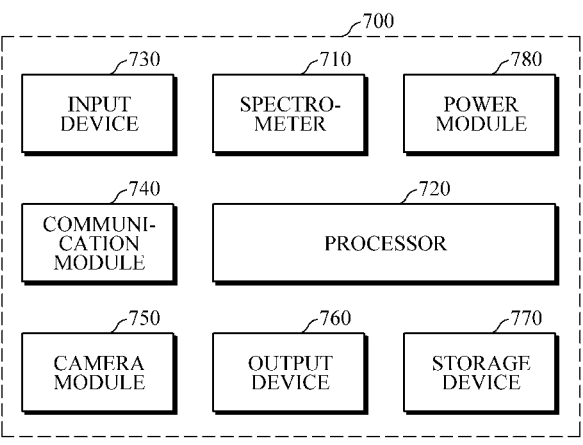
FIG. 7 is a block diagram illustrating an electronic device including an apparatus for estimating bio-information according to an example embodiment.

FIG. 7 is a block diagram illustrating an electronic device 700 including the apparatuses 100 and 500 for estimating bio-information, according to an example embodiment.

The electronic device 700 may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on IoT technology.

Referring to FIG. 7, the electronic device 700 may include a spectrometer 710, a processor 720, an input device 730, a communication module 740, a camera module 750, an output device 760, a storage device 770, and a power module 780. All the components of the electronic device 700 may be integrally mounted in a specific device or may be distributed in two or more devices. The spectrometer 710 and the processor 720 of FIG. 7 may include and/or may be similar in many respects to the spectrometers 110 and 510 and the processors 120 and 520 described above with reference to FIGS. 1 and 5, respectively, and may include additional features not mentioned above. Consequently, repeated descriptions of the spectrometer 710 and the processor 720 described above with reference to FIGS. 1 and 5 may be omitted for the sake of brevity.

The spectrometer 710 may be a laser spectrometer, in which a laser light source may emit light onto an object, and a detector may detect an optical signal by receiving light scattered or reflected from the object. For example, the object may be a body part, at which bio-information may be easily measured. For example, the object may be the skin of the wrist that is adjacent to the radial artery or a skin of the user where veins or capillaries are located. However, the object is not limited thereto and may be peripheral parts of the body, such as fingers, toes, and the like where blood vessels are densely distributed.

The spectrometer 710 may measure a spectrum from an object according to measurement conditions. For example, the measurement conditions may include an optical path length, a light source intensity for each wavelength of the spectrum, or detector noise characteristics for each wavelength of the spectrum, but are not limited thereto.

The processor 720 may execute programs, stored in the storage device 770, to control components connected (e.g., communicatively coupled) to the processor 720, and may perform various data processing or computation. The processor 720 may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The processor 720 may include the processors of the above apparatuses 100 and 500 for estimating bio-information. For example, in response to a request of a user for estimating bio-information, the processor 720 may transmit a control signal to the spectrometer 710, and may estimate bio-information using the spectrum received from the spectrometer 710.

In response to receiving the spectrum from the spectrometer 710, the processor 720 may calculate SNR values for each wavelength of the spectrum, may obtain a plurality of simulated absorbance spectra based on the calculated SNR values for each wavelength, and may derive an optimal wavelength combination for use in measuring bio-information based on the generated plurality of simulated absorbance spectra.

For example, the processor 720 may obtain noise equivalent absorbance for each wavelength based on the calculated SNR values for each wavelength, and may generate the plurality of simulated absorbance spectra based on the obtained noise equivalent absorbance for each wavelength.

Alternatively or additionally, the processor 720 may obtain, using the plurality of simulated absorbance spectra, the respective prediction values of a target component for each of a plurality of predetermined wavelength combinations. The processor 720 may calculate measurement performance for each wavelength combination based on the obtained plurality of prediction values for each wavelength combination, and may derive an optimal wavelength combination for use in the measurement based on the calculated measurement performance. For example, the measurement performance may be the LoD, and the processor 720 may calculate the LoD values based on a mean value or a standard deviation of the respective prediction values.

Alternatively or additionally, the processor 720 may calculate a statistical value of the LoD values for each wavelength combination, and may determine the optimal wavelength combination in ascending order of the calculated LoD values for each wavelength combination.

The processor 720 may estimate bio-information using the optimal wavelength combination. For example, the processor 720 may extract feature values for each wavelength included in the optimal wavelength combination, and may estimate blood glucose using the extracted feature values and a predefined blood glucose estimation model. For example, the predefined blood glucose estimation model may be defined as various linear or non-linear combination functions, such as addition, subtraction, division, multiplication, logarithmic value, regression equation, and the like, with no specific limitation.

The input device 730 may receive a command and/or data to be used by each component of the electronic device 700, from a user and the like. The input device 730 may include, for example, a microphone, a mouse, a keyboard, or a digital pen (e.g., a stylus pen, etc.).

The communication module 740 may support establishment of a direct (e.g., wired) communication channel and/or a wireless communication channel between the electronic device 700 and other electronic device, a server, or the spectrometer 710 within a network environment, and performing of communication via the established communication channel. The communication module 740 may include one or more communication processors that are operable independently from the processor 720 and supports a direct communication and/or a wireless communication.

The communication module 740 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 700 in a communication network using subscriber information (e.g., international mobile subscriber identity (IMSI), etc.) stored in a subscriber identification module.

The camera module 750 may capture still images or moving images. The camera module 750 may include a lens assembly having one more lenses, image sensors, image signal processors, and/or flashes. The lens assembly included in the camera module 750 may collect light emanating from a subject to be imaged.

The output device 760 may visually/non-visually output data generated or processed by the electronic device 700. The output device 760 may include a sound output device, a display device, an audio module, and/or a haptic module.

The sound output device may output sound signals to the outside of the electronic device 700. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device 700. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device 700 directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device 770 may store operating conditions required for operating the spectrometer 710, and various data required for other components of the electronic device 700. The various data may include, for example, software and input data and/or output data for a command related thereto. The storage device 770 may include a volatile memory and/or a non-volatile memory.

The power module 780 may manage power supplied to the electronic device 700. The power module may be implemented as least part of, for example, a power management integrated circuit (PMIC). The power module 780 may include a battery, which may include a primary cell which is not rechargeable, a secondary cell which is rechargeable, and/or a fuel cell.

Figure 8:
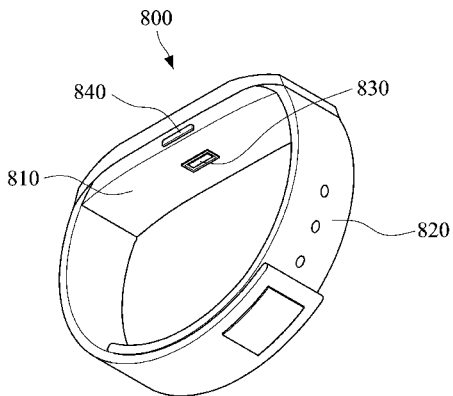
FIGS. 8 to 10 are diagrams illustrating examples of structures of an electronic device including an apparatus for estimating bio-information according to example embodiments.
Figure 9:
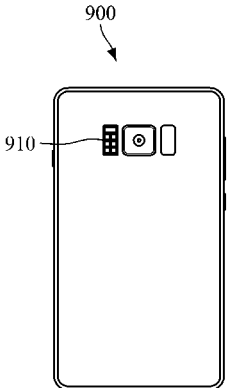
Figure 10:
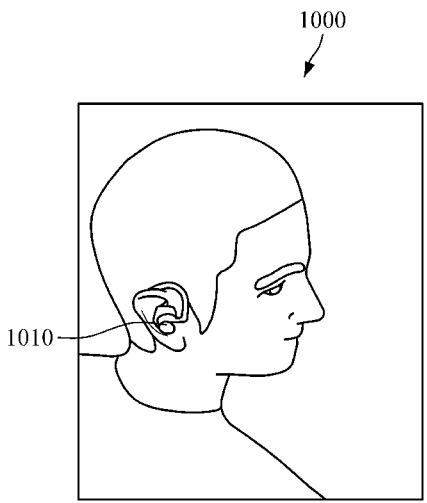

FIGS. 8 to 10 are diagrams illustrating examples of structures of the electronic device 700 including an apparatus for estimating bio-information according to example embodiments. Examples of the electronic device may include not only a smartphone, but also a smart watch, a smart band, smart glasses, a smart necklace, and an ear-wearable device, but the electronic device 700 is not limited thereto.

Referring to FIG. 8, the electronic device 700 may be implemented as a smartwatch wearable device 800, and may include a main body 810 and a strap 820.

The main body 810 may be formed in various shapes. A battery may be embedded in the main body 810 and/or the strap 820 to supply power to various components of the wearable device. The strap 820 may be connected to both ends of the main body to allow the main body to be worn on a wrist of the user, and may be flexible so as to be wrapped around the wrist of the user. The strap 820 may be composed of a first strap and a second strap which are separated from each other. One end of the first strap and of the second strap are connected to the main body 810, and the other ends thereof may be connected to each other via a fastening means. For example, the fastening means may be formed as magnetic fastening, Velcro fastening, pin fastening, and the like, but is not limited thereto. Further, the strap 820 is not limited thereto, and may be integrally formed as a non-detachable band.

The main body 810 may include the apparatus for estimating bio-information. A spectrometer 830, a processor, an output interface, a storage, and a communication interface may be mounted in the apparatus for estimating bio-information. However, depending on the size and shape of a form factor and the like, some of the display, the storage, and the communication interface may be omitted. The spectrometer 830 may include and/or may be similar in many respects to the spectrometers 110, 510, and 710 described above with reference to FIGS. 1, 5, and 7, and may include additional features not mentioned above. Consequently, repeated descriptions of the spectrometer 830 described above with reference to FIGS. 1, 5, and 7 may be omitted for the sake of brevity. In response to receiving a spectrum from the spectrometer 830, the processor may calculate SNR values for each wavelength of the spectrum, may generate a plurality of simulated absorbance spectra based on the calculated SNR values for each wavelength, may determine an optimal wavelength combination for use in measuring bio-information based on the generated plurality of simulated absorbance spectra, and may estimate bio-information using the determined optimal wavelength combination.

Referring back to FIG. 8, the manipulator 840 may be formed on a side surface of the main body 810, as illustrated herein. The manipulator 840 may receive a command of the user and may transmit the received command to the processor. Alternatively or additionally, the manipulator 840 may have a power button to turn the wearable device 800 on and/or off. A display is provided on a front surface of the main body 810, and may display various application screens, including heart rate information, blood glucose information, time information, received message information, and the like.

Referring to FIG. 9, the electronic device 700 may be implemented as a mobile device 900 such as a smartphone.

The mobile device 900 may include a housing and a display panel. The housing may form an exterior of the mobile device 900. The housing has a first surface, on which a display panel and a cover glass may be disposed sequentially, and the display panel may be exposed to the outside through the cover glass. A spectrometer 910, a camera module and/or an infrared sensor, and the like may be disposed on a second surface of the housing. The spectrometer 910 may include and/or may be similar in many respects to the spectrometers 110, 510, 710, and 830 described above with reference to FIGS. 1, 5, 7, and 8, and may include additional features not mentioned above. Consequently, repeated descriptions of the spectrometer 910 described above with reference to FIGS. 1, 5, 7, and 8 may be omitted for the sake of brevity. The spectrometer 910 may include one or more light sources and detectors. The spectrometer 910 may be mounted on the second surface, but is not limited thereto and may be formed in combination with a fingerprint sensor or a touch panel formed on the first surface of the housing. When a user transmits a request for estimating bio-information by executing an application and the like installed in the mobile device 900, the mobile device 900 may estimate bio-information using the spectrometer 910 and the processor in the mobile device 900, and may provide the estimated bio-information value as images and/or sounds to the user.

Referring to FIG. 10, the electronic device 700 may be implemented as an ear-wearable device 1000.

The ear-wearable device 1000 may include a main body and an ear strap. A user may wear the ear-wearable device 1000 by hanging the ear strap on the auricle. The ear strap may be omitted depending on a shape of the ear-wearable device 1000. The main body may be inserted into the external auditory meatus. A spectrometer 1010 may be mounted in the main body. The spectrometer 1010 may include and/or may be similar in many respects to the spectrometers 110, 510, 710, 830, and 910 described above with reference to FIGS. 1, 5, 7, 8, and 9, and may include additional features not mentioned above. Consequently, repeated descriptions of the spectrometer 1010 described above with reference to FIGS. 1, 5, 7, 8, and 9 may be omitted for the sake of brevity. Further, the ear-wearable device 1000 may provide the user with a bio-information estimation result as sound, or may transmit the estimation result to an external device, e.g., a mobile device, a tablet PC, etc., through a communication module provided in the main body.

The present disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be readily deduced by programmers of ordinary skill in the art to which the invention pertains.

The present disclosure has been described herein with regard to example embodiments. However, it will be understood that various changes and modifications can be made without changing technical conception and essential features of the present disclosure. Thus, it is clear that the above-described embodiments are illustrative in all aspects and are not intended to limit the present disclosure.

What is claimed is:

1. An apparatus for estimating bio-information, the apparatus comprising:
    a spectrometer configured to measure a spectrum from an object according to measurement conditions; and
    a processor configured to:
        obtain signal-to-noise ratio (SNR) values for each wavelength of the spectrum measured by the spectrometer,
        generate a plurality of simulated absorbance spectra based on the SNR values for each wavelength of the spectrum,
        obtain a plurality of prediction values based on the plurality of simulated absorbance spectra,
        calculate a Limit of Detection (LoD) value for each of a plurality of predetermined wavelength combinations, based on at least one of a mean value or a standard deviation of the plurality of prediction values,
        determine a wavelength combination from among the plurality of predetermined wavelength combinations having a minimum LoD value from among LoD values of the plurality of predetermined wavelength combinations,
        measure, using the spectrometer, spectrums of each wavelength of the determined wavelength combination within a predetermined measurement time for measuring the object,
        extract feature values for each wavelength of the determined wavelength combination,
        estimate, using a predefined estimation model, the bio-information based on the extracted feature values, and
        display, to a user of a device comprising the apparatus, the bio-information and an indication of whether the bio-information is outside of a predetermined range.

2. The apparatus of claim 1, wherein the spectrometer comprises:
    a light source configured to radiate light onto the object; and
    a detector configured to detect an optical signal by receiving light scattered or reflected from the object.

3. The apparatus of claim 1, wherein the measurement conditions comprise at least one of an optical path length, a light source intensity for each wavelength of the spectrum, and detector noise characteristics for each wavelength of the spectrum.

4. The apparatus of claim 1, wherein the processor is further configured to:
    obtain noise equivalent absorbance for each wavelength of the spectrum based on the SNR values for each wavelength of the spectrum, and
    generate the plurality of simulated absorbance spectra based on the noise equivalent absorbance for each wavelength of the spectrum.

5. The apparatus of claim 1, wherein the processor is further configured to obtain, based on the plurality of simulated absorbance spectra, prediction values of a target component for each of the plurality of predetermined wavelength combinations.

6. The apparatus of claim 5, wherein the processor is further configured to obtain the prediction values of the target component for each of the plurality of predetermined wavelength combinations by using at least one of linear regression analysis and component analysis by classical least squares (CLS).

7. The apparatus of claim 1, wherein the processor is further configured to:
    obtain, based on the LoD values for each of the plurality of predetermined wavelength combinations, a statistical value of the LoD values for each of the plurality of predetermined wavelength combinations, and
    determine the wavelength combination in ascending order of the LoD values for each of the plurality of predetermined wavelength combinations.

8. The apparatus of claim 1, wherein the wavelength combination is included in at least one of a combination band region and an overtone band region.

9. The apparatus of claim 1, wherein the bio-information comprises at least one of an antioxidant level, a blood glucose level, a blood pressure, a lactate level, an alcohol level, a cholesterol level, or a triglyceride level.

10. The apparatus of claim 1, wherein the processor is further configured to determine the plurality of predetermined wavelength combinations based on a position of the object and the bio-information to be estimated, and
    wherein the plurality of predetermined wavelength combinations comprise wavelengths in at least one of a combination band region, an overtone band region, or an overlap region comprising at least one wavelength in the combination band region and at least one wavelength in the overtone band region.

11. The apparatus of claim 10, wherein the wavelength combination comprises at least one wavelength in at least one of the combination band region, the overtone band region, or the overlap region.

12. The apparatus of claim 10, wherein wavelengths of the combination band region range from 2040 nanometers (nm) to 2380 nm, and
    wherein wavelengths of the overtone band region range from 1540 nm to 1820 nm.

13. A method of estimating bio-information, the method comprising:
    measuring a spectrum from an object according to measurement conditions;
    obtaining signal-to-noise ratio (SNR) values for each wavelength of the spectrum;
    generating a plurality of simulated absorbance spectra based on the SNR values for each wavelength of the spectrum;
    obtaining a plurality of prediction values based on the plurality of simulated absorbance spectra,
    calculate a Limit of Detection (LoD) value for each of a plurality of predetermined wavelength combinations, based on at least one of a mean value or a standard deviation of the plurality of prediction values,
    determining a wavelength combination from among the plurality of predetermined wavelength combinations having a minimum LoD value from among LoD values of the plurality of predetermined wavelength combinations;
    measuring spectrums of each wavelength of the determined wavelength combination within a predetermined measurement time for measuring the object;
    extracting feature values for each wavelength of the determined wavelength combination;
    estimating, using a predefined estimation model, the bio-information based on the extracted feature values; and displaying, to a user of a device, the bio-information and an indication of whether the bio-information is outside of a predetermined range.

14. The method of claim 13, wherein the measurement conditions comprise at least one of an optical path length, a light source intensity for each wavelength of the spectrum, and detector noise characteristics for each wavelength of the spectrum.

15. The method of claim 13, wherein the generating of the plurality of simulated absorbance spectra comprises:

obtaining noise equivalent absorbance for each wavelength of the spectrum based on the SNR values for each wavelength of the spectrum; and generating the plurality of simulated absorbance spectra based on the noise equivalent absorbance for each wavelength of the spectrum.

16. The method of claim 13, wherein the determining of the wavelength combination comprises obtaining prediction values of a target component for each of the plurality of predetermined wavelength combinations, based on the plurality of simulated absorbance spectra.

17. The method of claim 13, wherein the determining of the wavelength combination comprises:

obtaining a statistical value of the LoD values for each of the plurality of predetermined wavelength combinations, based on the LoD values for each of the plurality of predetermined wavelength combinations; and determining the wavelength combination in ascending order of the LoD values for each of the plurality of predetermined wavelength combinations.

18. The method of claim 13, wherein the wavelength combination is included in at least one of a combination band region and an overtone band region.

* * * * *